United States Patent

Böhner et al.

Patent Number: 4,640,703
Date of Patent: Feb. 3, 1987

[54] 2-PHENOXYPROPIONIC ACID CYANAMIDES AS HERBICIDES

[75] Inventors: Beat Böhner, Binningen; Hermann Rempfler, Ettingen; Rolf Schurter, Binningen, all of Switzerland

[73] Assignee: Ciba-Geigy Corporation, Ardsley, N.Y.

[21] Appl. No.: 676,962

[22] Filed: Nov. 30, 1984

[30] Foreign Application Priority Data

Dec. 6, 1983 [CH] Switzerland .......................... 6509/83
Apr. 18, 1984 [CH] Switzerland .......................... 1948/84

[51] Int. Cl.[4] .................. C07D 241/44; A01N 43/60; A01N 43/40; A01N 43/76
[52] U.S. Cl. ............................................. 71/92; 71/88; 71/90; 71/94; 71/105; 544/354; 546/157; 546/290; 546/291; 548/171; 548/221; 564/105
[58] Field of Search ........................... 544/354; 71/92

[56] References Cited

FOREIGN PATENT DOCUMENTS 2531643 10/1974 Fed. Rep. of Germany .
2433067 1/1976 Fed. Rep. of Germany .
2639796 3/1977 Fed. Rep. of Germany .
2640730 3/1978 Fed. Rep. of Germany .
3004770 8/1980 Fed. Rep. of Germany .

Primary Examiner—Mark L. Berch
Attorney, Agent, or Firm—Edward McC. Roberts; Kevin T. Mansfield; Irving M. Fishman

[57] ABSTRACT

2-Phenoxypropionic acid cyanamides of the formula

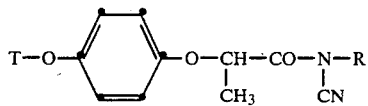

have a useful selective herbicidal activity against weeds, preferably grass weeds, in crops of useful plants.

In this formula
R is hydrogen, $C_1$–$C_4$alkyl, $C_3$–$C_4$alkenyl, $C_3$–$C_4$alkynyl or $C_2$–$C_4$alkoxyalkyl, and
T is a radical

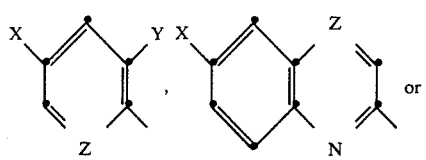

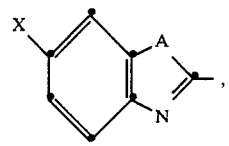

wherein
A is oxygen or sulfur,
X is fluorine, chlorine, bromine, iodine or trifluoromethyl,
Y is hydrogen, fluorine, chlorine, bromine or trifluormethyl, and
Z is nitrogen or the methine bridge.

16 Claims, No Drawings

2-PHENOXYPROPIONIC ACID CYANAMIDES AS HERBICIDES

The present invention relates to novel herbicidal 2-phenoxypropionic acid cyanamides, to the preparation thereof, to herbicidal compositions containing them as active ingredients, and to methods of using the novel compounds and compositions containing them for selectively controlling weeds in crops of cultivated plants. The invention further relates to novel intermediates for the synthesis of the compounds of this invention.

The 2-phenoxypropionic acid cyanamides of this invention are of the formula I

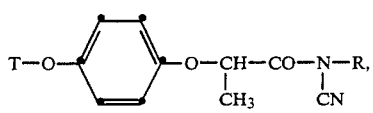

wherein
R is hydrogen, $C_1$–$C_4$alkyl, $C_3$–$C_4$alkenyl, $C_3$–$C_4$alkynyl or $C_2$–$C_4$alkoxyalkyl, and
T is a radical

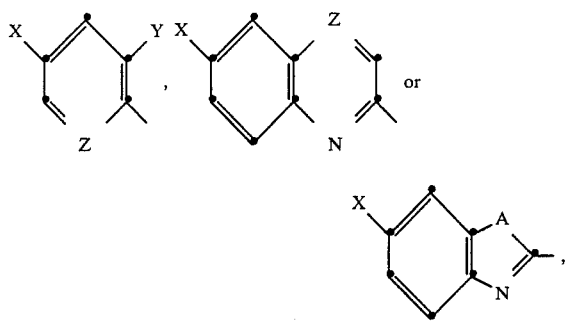

wherein
A is oxygen or sulfur,
X is fluorine, chlorine, bromine, iodine or trifluoromethyl,
Y is hydrogen, fluorine, chlorine, bromine or trifluoromethyl, and
Z is nitrogen or the methine bridge.

Herbicidal 2-phenoxypropionamides containing further substituents in the para-position of the phenyl nucleus are known from the literature, e.g. DE-OS Nos. 2 433 067, 2 531 643, 2 639 796, 2 640 730 or 3 004 770.

Surprisingly, it has now been found that the novel compounds of the present invention are superior to the compounds of this class described in the literature for selectively controlling weeds in crops of useful plants.

Within the scope of the present invention, the symbols R and T in the definition of formula I are for example the following substituents: R is generally hydrogen, methyl, ethyl, isopropyl, n-propyl, the four butyl isomers, or is allyl, methallyl, 2-butenyl, 3-butenyl, propargyl, 2-butynyl, 3-butynyl, methoxymethyl, methoxyethyl, ethoxymethyl or ethoxyethyl; and T is generally a radical selected from the group consisting of phenyl, 2-pyridinyl, 2-quinolinyl, 2-quinoxalinyl, 2-benzoxazolyl or 2 benzothiazolyl, which radical is substituted by at least the radical X. Preferably R is hydrogen or a saturated radical, e.g. $C_1$–$C_4$alkyl or $C_2$–$C_4$alkoxyalkyl and T is a radical such as 2-benzoxazolyl or 2-quinoxalinyl.

On account of their good selective herbicidal activity, particularly interesting compounds of formula I are those wherein either
(a) R is hydrogen or $C_1$–$C_4$alkyl, or
(b) T is the radical

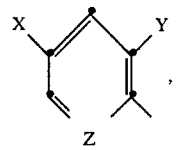

or
(c) T is the radical

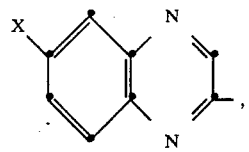

or
(d) T is the radical

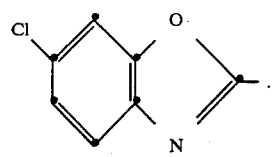

Among the compounds of subgroup (a), those compounds are preferred wherein R is $C_1$–$C_4$alkyl; among the compounds of subgroup (b), those compounds are preferred wherein either X is trifluoromethyl, Y is hydrogen and Z is the methine bridge; or X is trifluoromethyl, Y is hydrogen and Z is nitrogen; or X and Y are chlorine and Z is nitrogen; or X is chlorine, Y is fluorine and Z is nitrogen; i.e. T is a radical selected from the group consisting of 4-trifluoromethylphenyl, 5-trifluoromethylpyridin-2-yl, 3,5-dichloropyridin-2-yl and 5-chloro-3-fluoropyridin-2-yl.

Among the compounds of subgroup (c), those compounds are preferred wherein X is fluorine or chlorine.

Very particularly preferred subgroups of compounds of formula I are those wherein R is $C_1$–$C_4$alkyl and T is either 4-trifluoromethylphenyl or 5-trifluoromethylpyridin-2-yl or 3,5-dichloropyridin-2-yl or 5-chloro-3-fluoropyridin-2-yl, which last type is most particularly preferred; or wherein R is $C_1$–$C_4$alkyl and T is 6-fluoroquinoxalin-2-yl or 6-chloroquinoxalin-2-yl; or wherein R is $C_1$–$C_4$alkyl and T is 6-chlorobenzoxazol-2-yl.

Preferred individual compounds are e.g.:
2-[4-(5-chloro-3-fluoropyridin-2-yloxy)phenoxy]propionic acid N-cyano-N-methylamide,
2-[4-(5-trifluoromethylpyridin-2-yloxy)phenoxy]propionic acid N-cyano-N-methylamide,
2-[4-(5-chloro-3-fluoropyridin-2-yloxy)phenoxy]propionic acid N-cyano-N-ethylamide,
2-[4-(6-chloroquinoxalin-2-yloxy)phenoxy]propionic acid N-cyano-N-ethylamide, 2-[4-(6-chloroquinoxalin-2-yloxy)phenoxy]propionic acid N-cyano-N-methylamide,
2-[4-(6-fluoroquinoxalin-2-yloxy)phenoxy]phenoxy]- propionic acid N-cyano-N-ethylamide,
2-[4-(6-fluoroquinoxalin-2-yloxy)phenoxy]propionic acid N-cyano-N-methylamide or
2-[4-(6-chlorobenzoxazol-2-yloxy)phenoxy]propionic acid N-cyano-N-n-butylamide.

The compounds of formula I of this invention can be prepared by reacting a 2-phenoxypropionyl halide of formula II

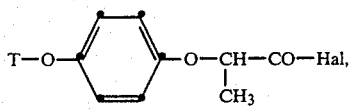
(II)

wherein T is as defined for formula I and Hal is chlorine or bromine, with a cyanamine of formula III

(III)

wherein R is as defined for formula I, in the presence of an acid acceptor.

If R has a meaning other than hydrogen, the compounds of subformula Ia

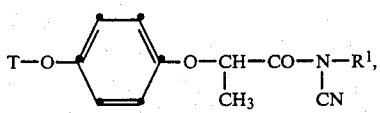
(Ia)

wherein T is as defined for formula I and $R^1$ is $C_1$-$C_4$alkyl, $C_3$-$C_4$alkenyl, $C_3$-$C_4$alkynyl or $C_2$-$C_4$alkoxyalkyl, can be obtained by reacting a corresponding cyanamino compound of subformula Ib

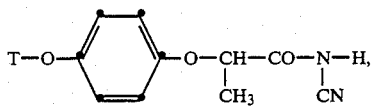
(Ib)

wherein T is as defined for formula I, with a halogen compound of formula IV

Hal—$R^1$ (IV), wherein $R^1$ is as defined for formula Ia and Hal is chlorine, bromine or iodine, in the presence of an acid acceptor.

In accordance with a second process, the compounds of formula I of this invention can also be obtained by reacting a phenoxypropionic acid derivative of formula V

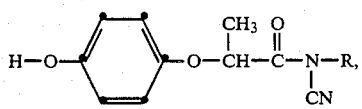
(V)

wherein R is as defined for formula I, with a halide of formula VI

T—Hal (VI), wherein T is as defined for formula I and Hal is fluorine, chlorine, bromine or iodine, in the presence of an acid acceptor.

In accordance with a third process, the compounds of formula I of this invention are obtained by reacting a propionic acid derivative of formula VII

(VII)

wherein R is as defined for formula I and Hal is chlorine, bromine, tosyl or mesyl, with a hydroquinone derivative of formula VIII

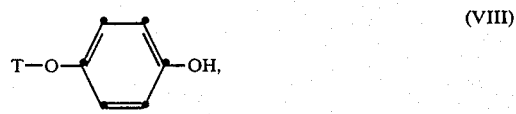
(VIII)

wherein T is as defined for formula I, in the presence of an acid acceptor.

The different reactions to obtain compounds of formula I or of formula Ia via formula Ib are conveniently carried out in aprotic, inert organic solvents. Examples of such solvents are: hydrocarbons such as benzene, toluene, xylene or cyclohexane; chlorinated hydrocarbons such as methylene chloride, chloroform, carbon tetrachloride, or chlorobenzene; ethers such as diethyl ether, ethylene glycol dimethyl ether, diethylene glycol dimethyl ether, tetrahydrofuran or dioxan; nitriles such as acetonitrile or propionitrile; amides such as dimethylformamide, diethylformamide or N-methylpyrrolidinone. The reaction temperatures are preferably in the range from $-20°$ to $+120°$ C. Preferred bases are tertiary amines such as trimethylamine, triethylamine, quinuclidine, 1,4-diazabicyclo[2.2.2]octane, 1,5-diazabicyclo[4.3.0]-non-5-ene or 1,8-diazabicyclo[5.4.-0]undec-7-ene. However, the bases employed may also be inorganic bases, e.g. hydrides such as sodium hydride and calcium hydride, hydroxides such as sodium hydroxide and potassium hydroxide, carbonates such as sodium and potassium carbonate, or bicarbonates such as potassium and sodium bicarbonate.

Most of the intermediates of formulae II, III, IV, VI and VIII are known or can be prepared by methods analogous to known ones.

The intermediates of formulae V and VII are novel and have been specially developed and prepared for the synthesis of compounds of formula I. Accordingly, they constitute a further object of the present invention.

The propionic acid derivative of formula VII

(VII)

is obtained by reacting a propionyl halide of formula IX

(IX)

wherein Hal is as defined for formula VII and Hal¹ is chlorine or bromine, with a cyanamine of formula X

  (X)

wherein R is as defined for formula VII, in the presence of an acid acceptor.

In accordance with a variant of the above process, the compounds of subformula VIIa

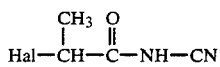  (VIIa)

can also be prepared by first reacting the propionyl halide of formula IX with a cyanamine of formula XI

  (XI), in the presence of an acid acceptor, and, if desired, reacting these compounds of formula VIIa with an alkylating agent which introduces the radical R¹ as defined for formula IV.

The intermediates of formula V can be prepared from compounds of formula VII by reacting the compound of formula VII

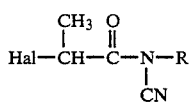  (VII)

with 4-benzyloxyphenol, in the presence of a base, and treating the resultant product of formula XII

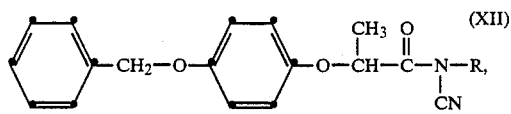  (XII)

wherein R is as defined for formula I, with hydrogen, in the presence of a hydrogenation catalyst, e.g. palladium on carbon.

The starting materials of formula IX, X or XI are known or can be prepared by known methods. The novel intermediates of formula XII have been specially developed and prepared for the synthesis of compounds of formula I. They likewise constitute a further object of this invention.

The preparation of the novel intermediates of formulae V and VII is carried out according to methods known per se. The reaction conditions are in each case chosen in accordance with the requirements of the reagents employed.

Compounds of subformula Ic

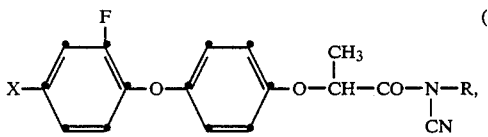  (Ic)

wherein R and X are as defined for formula I, can be prepared by a novel process which comprises either (a) reacting a 3-nitropyridine of formula XIII

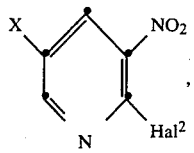  (XIII)

wherein X is as defined for formula I and Hal² is fluorine, chlorine or bromine, with hydroquinone, in the presence of a base, to give a compound of formula XIV

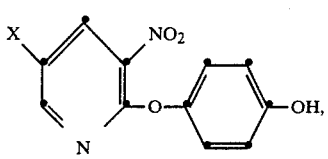  (XIV)

reducing this intermediate, in the presence of a metal catalyst, to give an amino compound of formula XV

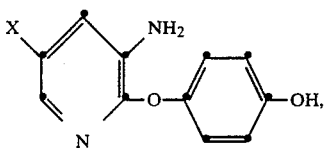  (XV)

diazotising this amino compound and converting it with a fluorinating agent into a compound of formula XVI

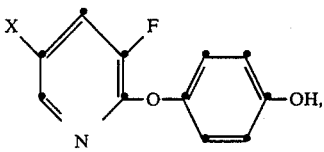  (XVI)

and reacting this fluorinated intermediate with a propionic acid derivative of formula VII, in the presence of a base, or by (b) reacting the nitropyridine of formula XIII with a propionic acid ester of formula XVII

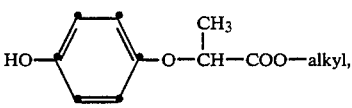  (XVII)

wherein alkyl is C₁–C₄alkyl, in the presence of a base, reducing the resultant intermediate of formula XVIII

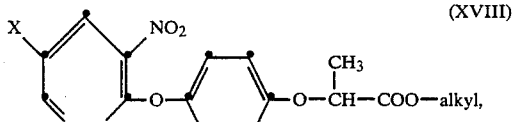  (XVIII)

in the presence of a metal catalyst, to give the amino compound of formula XIX

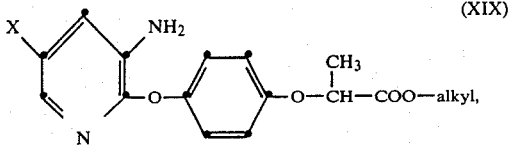

diazotising this intermediate and converting it with a fluorinating agent into a compound of formula XX

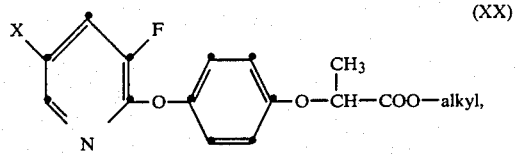

saponifying this ester and converting it with a halogenating agent into a 2-phenoxypropionyl halide of subformula IIa

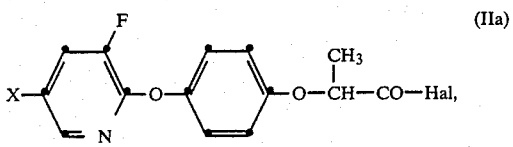

wherein Hal and X are as defined for formula II, and reacting said 2-phenoxypropionyl halide with a cyanamine of formula III, in the presence of a base.

In accordance with a variant of the above process, the intermediates of formula XVIII can also be obtained by reacting the compounds of formula XIV with a propionic acid ester of formula XXI

wherein Hal is chlorine or bromine and alkyl is $C_1$-$C_4$alkyl, in the presence of a base.

The reaction conditions for these per se known reaction steps, e.g. catalysts, solvents and reaction temperatures, are known from the literature.

The starting materials of formulae XIII and XVII are known

The intermediates of formulae XIV, XV and XVIII are novel and have been specially developed for the synthesis of compounds of formula Ic. Said intermediates and the novel process together with variants a and b likewise constitute objects of the present invention. The compounds of formula IIa, wherein X is halogen, are also novel and constitute a further object of this invention.

The compounds of formula I are obtained as racemates. Both enantiomers of the compounds of formula I and mixtures thereof constitute an object of the invention. Unless a particular isomer is expressly mentioned, what is said in the description always refers to the racemates.

The compounds of formula I are stable compounds and no protective measures are required for handling them.

When used at low rates of application, the compounds of formula I have good selective herbicidal properties, in particular against monocot weeds, which make them most suitable for use in crops of useful dicot plants, in particular cotton, soybeans, rape, sugar beet, fodder beet and sunflowers. Some of the compounds of formula I of the invention can also be used as selective herbicides in crops of monocot plants such as cereals, e.g. wheat and barley. In some cases damage is also caused to weeds which have only been controlled up to now with total herbicides.

When used higher rates of application, the compounds of formula I act as total herbicides.

The selective herbicidal activity of the compounds of the invention is observed both in pre- and postemergence application. Accordingly, these compounds can be used with equally good sucess for selectively controlling weeds, in particular grass weeds, pre- and postemergence.

The invention also relates to herbicidal compositions containing a novel compound of formula I and to methods of controlling monocot weeds, in particular grasses, pre- and postemergence.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils, epoxidised vegetable oils such as epoxidised coconut oil or soybean oil, or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood N.J., 1981; H. Stache, "Tensid-Taschenbuch", 2nd Edition, C. Hanser Verlag, Munich and Vienna, 1981; M. and J. Ash, "Encyclopedia of Surfactants", Vol. I–III, Chemical Publishing Co., New York, 1980–81.

The herbicidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

EMULSIFIABLE CONCENTRATES active ingredient: 1 to 20%, preferably 5 to 10%
surfactant: 5 to 30%, preferably 10 to 20%
liquid carrier: 50 to 94%, preferably 70 to 85%

DUSTS active ingredient: 0.1 to 10%, preferably 0.1 to 1%
solid carrier: 99.9 to 90%, preferably 99.9 to 99%

SUSPENSION CONCENTRATES active ingredient: 5 to 75%, preferably 10 to 50%
water: 94 to 25%, preferably 90 to 30%
surfactant: 1 to 40%, preferably 2 to 30%

WETTABLE POWDERS active ingredient: 0.5 to 90%, preferably 1 to 80%
surfactant: 0.5 to 20%, preferably 1 to 15%
solid carrier: 5 to 95%, preferably 15 to 90%

GRANULATES active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

PREPARATORY EXAMPLES

Example P1

2-[4-(4-Trifluoromethylphenoxy)phenoxy]propionic acid N-cyanamide (compound 1.4)

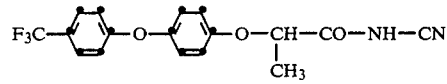

10.4 g (0.1575 mole) of 85% potassium hydroxide are dissolved in 75 ml of water. 3.5 g (0.0825 mole) of cyanamide are added at 20° C. and the clear, colourless solution is cooled to 10° C. Then a solution of 25.8 g (0.075 mole) of 2-[4-(4-trifluoromethylphenoxy)phenoxy]propionyl chloride in 15 ml of acetone is added dropwise such that the temperature does not exceed 15° C. After the reaction mixture has been stirred for 45 minutes at this temperature, 9 g (0.09 mole) of 37% aqueous hydrochloric acid are added dropwise at 5° C. The product precipitates as an oil which crystallises on standing over 30 minutes. The colourless crystals are isolated by filtration, washed with water, dried over phosphorous pentoxide, affording 24.9 g (95.0% of theory) of 2-[4-(4-trifluoromethylphenoxy)phenoxy]-propionic acid N-cyanamide with a melting point of 125°–127° C.

Example P2

2-[4-(4-Trifluoromethylphenoxy)phenoxy]propionic acid N-cyano-N-methylamide (compound 1.3)

17.5 g (0.05 mole) of 2-[4-(4-trifluoromethylphenoxy)phenoxy]propionic acid N-cyanamide are dissolved in 60 ml of methylethyl ketone and with 7.6 g (0.055 mole) of potassium carbonate heated for 30 minutes to reflux. Then 3.6 ml (0.057 mole) of methyl iodide are added at 30° C. to the colourless suspension and the mixture is stirred for two hours at the same temperature. The reaction mixture is then filtered and the filtrate is concentrated by evaporation. The oily residue is chromatographed through silica gel eluted with petroleum ether-/ethyl acetate (3:1) and the main fraction is concentrated by evaporation, affording 10.9 g (59.9% of theory) of 2-[4-(4-trifluoromethylphenoxy)phenoxy]propionic acid N-cyano-N-methylamide as a clear, colourless oil with a refractive index of $n_D^{23} = 1.5228$.

Example P3

2-[4-(6-Chlorobenzoxazol-2-yloxy)phenoxy]propionic acid N-cyano-N-butylamide (compound 2.4)

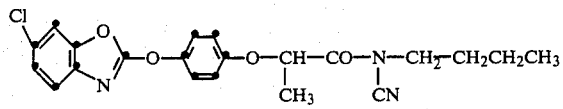

(a)

2-Bromopropionic acid N-cyano-N-methylamide 10.5 g (0.25 mole) of cyanamide are dissolved in 250 ml of 2N potassium hydroxide solution and the solution so obtained is cooled to +10° C. At this temperature 26.5 ml (0.25 mole) of 2-bromopropionyl bromide are added dropwise and the reaction mixture is stirred for one hour at the same temperature. Then 16.8 g (0.2 mole) of sodium bicarbonate are added. 63 g (0.5 mole) of dimethylsulfate are subsequently added dropwise at 20° C. and the reaction mixture is stirred for 4 hours and extracted with methylene chloride. The combined orgnaic phases are dried over sodium sulfate and concentrated by evaporation, affording as residue 27.5 g of crude product. Vacuum distillation of this crude products yields 13.6 g (28.5% of theory) of 2-bromopropionic acid N-cyano-N-methylamide with a boiling point of 45°–47° C. at 0.008 mbar.

(b)

2-(4-Benzyloxyphenoxy)propionic acid N-cyano-N-methylamide

With efficient stirring, 19.1 g (0.1 mole) of 2-bromopropionic acid N-cyano-N-methylamide are added dropwise to a solution of 20.0 g (0.1 mole) of hydroquinone monobenzyl ether and 16.5 g (0.12 mole) of potassium carbonate in 200 ml of dimethylformamide. After the slightly exothermic reaction has subsided, the reaction mixture is heated for 3 hours to 40° C. The precipitated salts are then removed by filtration and the filtrate is concentrated by evaporation. The residue is dissolved in ether and the ether solution is extracted with dilute sodium hydroxide solution. The organic phase is dried over sodium sulfate, the solvent is evaporated off and the residue is distilled in vacuo, affording 19.5 g (63% of theory) of 2-(4-benzyloxyphenoxy)propionic acid N-cyano-N-methylamide with a melting point of 56°–58° C.

(c)

2-(4-Hydroxyphenoxy)propionic acid N-cyano-N-butylamide 16.5 g (0.047 mole) of 2-(4-benzyloxyphenoxy)propionic acid N-cyano-N-butylamide, prepared according to Example b), are hydrogenated with hydrogen in 170 ml of dioxan, in the presence of 1.7 g of 5% palladium on carbon catalyst. The catalyst is then removed by filtration and the filtrate is concentrated by evaporation. The residue is chromatographed through silica gel eluted with ethyl acetate/hexane (1:3), affording 7.5 g (61% of theory) of 2-(4-hydroxyphenoxy)propionic acid N-cyano-N-butylamide as a colourless oil. $n_D^{25}$: 1.5132.

(d)

4.4 g (0.017 mole) of 2-(hydroxyphenoxy)propionic acid N-cyano-N-butylamide, 3.8 g (0.02 mole) of 2,6-dichlorobenzoxazole and 3.5 g (0.025 mole) of potassium carbonate are stirred in 50 ml of acetonitrile for 10 hours at room temperature. The salts are then removed by filtration and the filtrate is concentrated by evaporation. The residue is chromatographed through silica gel eluted with ethyl acetate/hexane (1:3), affording 2-[4-(6-chlorobenzoxazol-2-yloxy)phenoxy]propionic acid N-cyano-N-butylamide with a melting point of 91°–92° C.

Example P4

2-Bromopropionic acid N-cyano-N-butylamide 29.5 g (0.137 mole) of 2-bromopropionyl bromide are added dropwise at 15° C. to 13.4 g (0.137 mole) of butyl cyanamide and 13.8 g (0.137 mole) of triethylamine in 150 ml of ether. The mixture is stirred for 3 hours at 20° to 25° C., then filtered to remove the precipitated salt. The filtrate is extracted with dilute hydrochloric acid and the extract is dried over sodium sulfate and concentrated by evaporation. The oily residue is distilled under high vacuum, affording 22.6 g (70.8% of theory) of 2-bromopropionic acid N-cyano-N-butylamide with a boiling point of 53°–54° C. at 0.0052 mbar.

Example P5

2-[4-(5-Chloro-3-fluoropyridin-2-yloxy)phenoxy]propionic acid N-cyano-N-methylamide (compound 1.26)

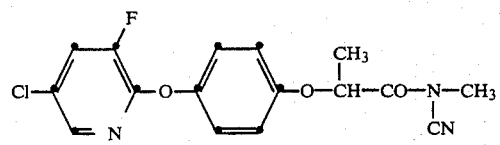

(a)

4-(5-Chloro-3-nitropyridin-2-yloxy)phenol

A mixture of 85.9 g (0.78 mole) of hydroquinone, 1200 ml of acetonitrile and 53.9 g (0.39 mole) of potassium carbonate is heated to 60° C., then a solution of 115.8 g (0.60 mole) of 2,5-dichloro-3-nitropyridine in 500 ml of acetonitrile is added dropwise over 6 hours and the mixture is stirred for 36 hours. The solvent is removed by distillation and the residue is poured into a mixture of ice-water and hydrochloric acid. After extraction with methylene chloride, the combined organic phases are dried over magnesium sulfate, treated with activated carbon, filtered and concentrated. The residue is purified by crystallisation in a mixture of hexane and ethyl acetate, affording 99 g (62% of theory) of 4-(5-chloro-3-nitropyridin-2-yloxy)phenol with a melting point of 125°–126° C.

(b)

4-(3-Amino-5-chloropyridin-2-yloxy)phenol 110.7 g (0.415 mole) of 4-(5-chloro-3-nitropyridin-2-yloxy)phenol are dissolved in 1200 ml of dioxan and, after addition of 22.0 g of Raney nickel catalyst, hydrogenated with hydrogen at 20°–25° C. The catalyst is then removed by filtration, the solution is concentrated and the residue is stirred in hexane and the product is filtered and dried, affording 96.0 g (98% of theory) of 4-(3-amino-5-chloropyridin-2-yloxy)phenol with a melting point of 174° C.

(c)

4-(5-Chloro-3-fluoropyridin-2-yloxy)phenol 122.5 g (0.518 mole) of 4-(3-amino-5-chloropyridin-2-yloxy)phenol are introduced at −8° to 0° C. into a vessel charged with 400 g (20 moles) of hydrogen fluoride. Then 37.3 g (0.540 mole) of sodium nitrite are added in portions over one hour. The mixture is stirred for 2 hours at 0° C. and slowly heated to 55° C. in an autoclave. Excess hydrogen fluoride is removed by distillation and the residue is taken up in 200 ml of methylene chloride and the solution is neutralised with ice-water and ammonia, the organic phase is dried and concentrated by evaporation, affording 112 g of 4-(5-chloro-3-fluoropyridin-2-yloxy)phenol with a melting point of 97°–98° C.

(d)

48.0 g (0.20 mole) of 4-(5-chloro-3-fluoropyridin-2-yloxy)phenol and 38.2 g (0.20 mole) of 2-bromopropionic acid N-cyano-N-methylamide are dissolved in 400 ml of acetonitrile. 35.9 g (0.26 mole) of potassium carbonate and 0.33 g (0.002 mole) of potassium iodide are added to the solution and the reaction mixture is heated for 13 hours to 80° C. The precipitate is removed by filtration, the filtrate is concentrated by evaporation and the residue is taken up in 500 ml of methylene chloride. The solution is purified by treatment with activated carbon and filtration through silica gel. The filtrate is concentrated by evaporation and the residue is crystallised from a mixture of hexane and ethyl acetate, affording 61 g of 2-[4-(5-chloro-3-fluoropyridin-2-yloxy)phenoxy]propionic acid N-cyano-N-methylamide.

Example P6

2-[4-(5-Chloro-3-fluoropyridin-2-yloxy)phenoxy]propionic acid N-n-butyl-N-cyanamide (compound 1.28)

(a)

Methyl 2-[4-(5-chloro-3-nitropyridin-2-yloxy)phenoxy]propionate 38.6 g (0.20 mole) of 2.5-dichloro-3-nitropyridine, 41.2 g (0.21 mole) of methyl 2-(4-hydroxyphenoxy)propionate, 400 ml of acetonitrile, 35.9 g (0.26 mole) of potassium carbonate and 0.33 g (0.002 mole) of potassium iodide are heated for 13 hours to 80° C. The reaction mixture is filtered and the filter cake is washed with acetonitrile. The filtrate is concentrated by evaporation and the residue is taken up in 500 ml of methlyene chloride. After treating the solution with 15 g of activated carbon, it is filtered through a layer of silica gel and the filtrate is concentrated by evaporation. The residue is crystallised from a mixture of hexane and ethyl acetate, affording 65.7 g (93.1% of theory) of methyl 2-[4-(5-chloro-3-nitropyridin-2-yloxy)phenoxy]propionate with a melting point of 91°–92° C.

(b)

Methyl 2-[4-(3-amino-5-chloropyridin-2-yloxy)phenoxy]propionate 190.8 g (0.541 mole) of methyl 2-[4-(5-chloro-3-nitropyridin-2-yloxy)phenoxy]propionate are dissolved in 1.9 l of dioxan. 40 g of Raney nickel catalyst are added and hydrogenation is effected with hydrogen at 20°–25° C. The catalyst is then removed by filtration, the solvent is distilled off and the still warm oily residue is crystallised by stirring it in hexane. The crystalline precipitate is isolated by filtration and dried, affording 167.4 g (96% of theory) of methyl 2-[4-(3-amino-5-chloropyridin-2-yloxy)phenoxy]propionate with a melting point of 92°–94° C.

(c)

Methyl 2-[4-(5-chloro-3-fluoropyridin-2-yloxy)phenoxy]propionate

A vessel is charged with 400 g (20 moles) of hydrogen fluoride and 167.4 g (0.518 mole) of methyl 2-[4-(3-amino-5-chloropyridin-2-yl-oxy)phenoxy]propionate are added in portions at a temperature from −8° to 0° C. 37.3 g (0.540 mole) of sodium nitrate are added over one hour and the mixture is stirred for two hours before it is slowly heated in an autoclave to 55° C. Excess hydrogen fluoride is removed by distillation and the residue is taken up in a mixture of 200 ml of methylene chloride and ice-water and the solution is neutralised with concentrated ammonia. The neutralised solution is extracted three times with methylene chloride and the organic extracts are washed with water, dried and concentrated by evaporation, affording 81.0 g (48% of theory) of methyl 2-[4-(5-chloro-3-fluoropyridin-2-yloxy)phenoxy]propionate with a melting point of 63°–64°.

(d)

2-[4-(5-Chloro-3-fluoropyridin-2-yloxy)phenoxy]propionic acid

A mixture of 67.0 g (0.206 mole) of methyl 2-[4-(5-chloro-3-fluoropyridin-2-yloxy)phenoxy]propionate, 350 ml of dioxan and 250 ml of 1N sodium hydroxide solution is stirred for 2 hours at 40° C. The reaction mixture is poured into a mixture of ice and 150 ml of 2N hydrochloric acid and extracted twice with ethyl acetate. The extracts are washed with a saturated solution of sodium chloride, dried over magnesium sulfate, filtered and concentrated by evaporation, affording 63.6 g (99% of theory) of 2-[4-(5-chloro-3-fluoropyridin-2-yloxy)phenoxy]propionic acid with a melting point of 95°–97° C.

(e)

2-[4-(5-Chloro-3-fluoropyridin-2-yloxy)phenoxy]propionyl chloride 63.6 g of 2-[4-(5-chloro-3-fluoropyridin-2-yloxy)phenoxy]propionic acid are dissolved in 700 ml of toluene, then 200 ml of toluene are removed from this solution by distillation. After cooling to 90° C., 25 ml (0.34 mole) of thionyl chloride are added dropwise and the solution is stirred for 14 hours at this temperature. The reaction mixture is then concentrated to a volume of 200 ml and the resultant solution of 2-[4-(5-chloro-3-fluoropyridin-2-yloxy)phenoxy]propionyl chloride in toluene is used direct for the following reaction step.

(f)

While cooling with ice, a solution of 9.9 g (0.030 mole) of 2-[4-(5-chloro-3-fluoropyridin-2-yloxy)phenoxy]propionyl chloride in 30 ml of toluene is added dropwise to a solution of 3.5 g (0.035 mole) of triethylamine and 3.2 g (0.033 mole) of n-butylcyanamine in 40 m of toluene. After 5 hours, the precipitate is removed by filtration and the filtrate is purified by chromatography through silica gel. The eluate is concentrated by evaporation, affording 2-[4-(5-chloro-3-fluoropyridin-2-yloxy)phenoxy]propionic acid N-n-butyl-N-cyanamide as a yellowish oil. $n_D^{25}$: 1.5482.

Example P7

2R-[4-(5-Chloro-3-fluoropyridin-2-yloxy)phenoxy]propionic acid N-ethyl-N-cyanamide While cooling with ice, a solution of 4.43 g (0.030 mole) of 1,8-diazabicyclo[5.4.0]undec-7-ene (97%) in 10 ml of acetonitrile is added dropwise to a solution of 2.1 g (0.030 mole) of ethylcyanamine and 9.9 g (0.030 mole) of 2R-[4-(5-chloro-3-fluoropyridin-2-yloxy)phenoxy]propionyl chloride (m.p. 47°–48° C.) in 30 ml of acetonitrile. After 4 hours, the reaction mixture is concentrated. The desired 2R-[4-(5-chloro-3-fluoropyridin-2-yloxy)phenoxy]propionic acid N-ethyl-N-cyanamide is obtained by chromatographing the residue through silica gel and concentrating the eluate (solvent mixture: ethyl acetate/hexane 1:1) by evaporation.

Example P8

2-[4-(6-Fluoroquinoxalin-2-yloxy)phenoxy]propionic acid N-cyan-N-ethylamide (compound 3.18)

10 g (0.039 mole) of 4-(6-fluoroquinoxalin-2-yloxy)phenol, 9.6 g (0.047 mole) of 2-bromopropionic acid N-cyano-N-ethylamide and 8.1 g (0.058 mole) of potassium carbonate are stirred for 14 hours at room temperature in 100 ml of acetonitrile. The precipitated salts are removed by filtration and the filtrate is concentrated by evaporation. The residue is chromatographed through silica gel eluted with ethyl acetate/hexane (1:3), affording 7.1 g (48% of theory) of 2-[4-(6-fluoroquinoxalin-2-yloxy)phenoxy]propionic acid N-cyano-N-ethylamide with a melting point of 108°–111° C.

The intermediates and compounds of formula I listed in the following tables are obtained in analogous manner.

TABLE 1

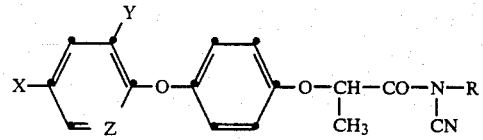

| Compound No. | X | Y | Z | R | Physical data |
|---|---|---|---|---|---|
| 1.1 | CF₃ | H | N | CH₃ | $n_D^{23}$: 1.5210 |
| 1.2 | CF₃ | H | N | H | m.p.: 137–138° C. |
| 1.3 | CF₃ | H | CH | CH₃ | $n_D^{23}$: 1.5228 |
| 1.4 | CF₃ | H | CH | H | m.p.: 125–127° C. |
| 1.5 | Cl | Cl | N | CH₃ | m.p.: 89–90° C. |
| 1.6 | Cl | Cl | N | H | $n_D^{23}$: 1.5574 |
| 1.7 | Cl | Cl | N | C₂H₅ | |
| 1.8 | Cl | Cl | N | C₄H₉—n | |
| 1.9 | Cl | Cl | N | —CH₂—CH=CH₂ | |
| 1.10 | Cl | Cl | N | —(CH₂)₂—OCH₃ | |
| 1.11 | CF₃ | H | N | C₂H₅ | m.p. 50–55° C. |
| 1.12 | CF₃ | H | N | C₄H₉—n | |
| 1.13 | CF₃ | H | N | —CH₂CH=CH₂ | |
| 1.14 | CF₃ | H | N | —(CH₂)₂—OCH₃ | $n_D^{31}$: 1.5122 |
| 1.15 | CF₃ | H | CH | C₂H₅ | |
| 1.16 | CF₃ | H | CH | C₄H₉ | |
| 1.17 | CF₃ | H | CH | —CH₂—CH=CH₂ | m.p. 79–80° C. |
| 1.18 | CF₃ | H | N | —(CH₂)₂—OCH₃ | |
| 1.19 | CF₃ | Cl | N | H | m.p. 93–94° C. |
| 1.20 | CF₃ | Cl | N | CH₃ | m.p. 94–95° C. |
| 1.21 | CF₃ | Cl | N | C₂H₅ | |
| 1.22 | CF₃ | Cl | N | C₄H₉—n | $n_D^{25}$: 1.5180 |
| 1.23 | CF₃ | Cl | N | —CH₂—CH=CH₂ | |
| 1.24 | CF₃ | Cl | N | —(CH₂)₂—OC₃ | $n_D^{31}$: 1.5162 |
| 1.25 | Cl | F | N | H | |
| 1.26 | Cl | F | N | CH₃ | |
| 1.27 | Cl | F | N | C₂H₅ | $n_D^{25}$: 1.5545 |
| 1.28 | Cl | F | N | C₄H₉—n | $n_D^{25}$: 1.5482 |
| 1.29 | Cl | F | N | —CH₂—CH=CH₂ | |
| 1.30 | Cl | F | N | —(CH₂)₂—OCH₃ | |

TABLE 2

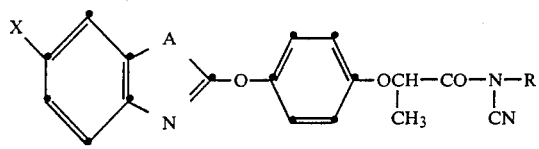

| Compound No. | A | X | R | Physical data |
|---|---|---|---|---|
| 2.1 | O | Cl | H | |
| 2.2 | O | Cl | CH₃ | |
| 2.3 | O | Cl | C₂H₅ | |
| 2.4 | O | Cl | C₄H₉—n | m.p. 91–92° C. |
| 2.5 | O | Cl | —CH₂—CH=CH₂ | |
| 2.6 | O | Cl | —(CH₂)₂—OCH₃ | |
| 2.7 | O | Cl | —CH₂—C≡CH | |
| 2.8 | S | Cl | H | |
| 2.9 | S | Cl | CH₃ | |
| 2.10 | S | Cl | C₂H₅ | |
| 2.11 | S | Cl | C₄H₉—n | |
| 2.12 | S | Cl | —CH₂—CH=CH₂ | |
| 2.13 | S | Cl | —(CH₂)₂—OCH₃ | |
| 2.14 | O | F | H | |
| 2.15 | O | F | CH₃ | |
| 2.16 | S | F | H | |
| 2.17 | S | F | CH₃ | |
| 2.18 | O | CF₃ | H | |
| 2.19 | O | CF₃ | CH₃ | |

TABLE 3

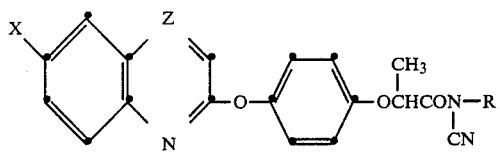

| Compound No. | X | Z | R | Physical data |
|---|---|---|---|---|
| 3.1 | Cl | N | H | m.p. 152–154° C. |
| 3.2 | Cl | N | CH₃ | m.p. 106–108° C. |
| 3.3 | Cl | N | C₂H₅ | m.p. 106–111° C. |
| 3.4 | Cl | N | C₄H₉—n | m.p. 62–65° C. |
| 3.5 | Cl | N | —CH₂—CH=CH₂ | |
| 3.6 | Cl | N | —(CH₂)₂—OCH₃ | $n_D^{40}$: 1.5794 |
| 3.7 | Cl | CH | H | |
| 3.8 | Cl | CH | CH₃ | |
| 3.9 | Cl | CH | C₂H₅ | |
| 3.10 | Cl | CH | C₄H₉—n | |
| 3.11 | Cl | CH | —CH₂—CH=CH₂ | |
| 3.12 | Cl | CH | —(CH₂)₂—OCH₃ | |
| 3.13 | F | N | H | m.p. 167–169° C. |
| 3.14 | F | N | CH₃ | m.p. 141–143° C. |
| 3.15 | F | CH | H | |
| 3.16 | F | CH | CH₃ | |
| 3.17 | F | N | C₄H₉—n | m.p. 94–95° C. |
| 3.18 | F | N | C₂H₅ | m.p. 108–111°C. |

TABLE 4

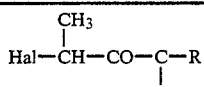

| Compound No. | Hal | R | Physical data |
|---|---|---|---|
| 4.1 | Br | H | |
| 4.2 | Br | CH₃ | b.p. 45–47° C./0.008 mbar |
| 4.3 | Cl | H | |
| 4.4 | Cl | CH₃ | |
| 4.5 | Cl | C₄H₉—n | |
| 4.6 | Br | C₄H₉—n | b.p. 53–54° C./0.0052 mbar |
| 4.7 | Br | C₂H₅ | b.p. 40–45° C./0.0075 mbar |
| 4.8 | Br | —(CH₂)₂—OCH₃ | b.p. 85° C./0.02 mbar |

TABLE 5

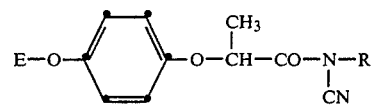

| Compound No. | E | R | Physical data |
|---|---|---|---|
| 5.1 | benzyl | H | |
| 5.2 | benzyl | CH₃ | m.p. 56–58° C. |
| 5.3 | benzyl | C₂H₅ | m.p. 57–63° C. |
| 5.4 | benzyl | C₄H₉—n | m.p. 108–109° C. |
| 5.5 | H | H | |
| 5.6 | H | CH₃ | oil |
| 5.7 | H | C₂H₅ | |
| 5.8 | H | C₄H₉—n | $n_D^{25}$: 1.5132 |

TABLE 6

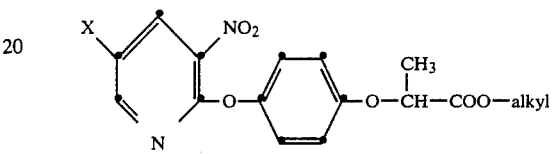

| Compound No. | X | Alkyl | Physical data |
|---|---|---|---|
| 6.1 | Cl | CH₃ | m.p. 91–92° C. |
| 6.2 | Br | CH₃ | |
| 6.3 | F | CH₃ | |
| 6.4 | Cl | C₂H₅ | |
| 6.5 | Cl | C₄H₉—n | |
| 6.6 | CF₃ | CH₃ | |
| 6.7 | CF₃ | C₄H₉—n | |

TABLE 7

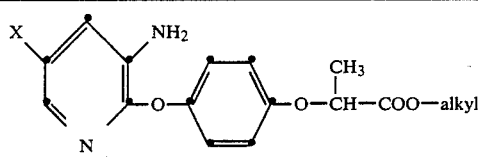

| Compound No. | X | Alkyl | Physical data |
|---|---|---|---|
| 7.1 | Cl | CH₃ | m.p. 92–94° C. |
| 7.2 | Br | CH₃ | |
| 7.3 | F | CH₃ | |
| 7.4 | Cl | C₂H₅ | |
| 7.5 | Cl | C₄H₉—n | oil |
| 7.6 | CF₃ | CH₃ | |
| 7.7 | CF₃ | C₄H₉—n | |

TABLE 8

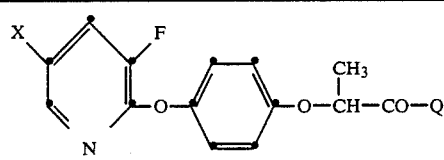

| Compound No. | X | Q | Physical data |
|---|---|---|---|
| 8.1 | Cl | OH | m.p. 95–97° C. |
| 8.2 | Cl | ONa | |
| 8.3 | Cl | OH | |
| 8.4 | Br | OH | |
| 8.5 | F | OH | |
| 8.6 | CF₃ | OH | |
| 8.7 | Cl | Cl | oil |
| 8.8 | Cl | Br | |

TABLE 8-continued

[Structure: X and F substituted pyridine connected via O to phenyl ring with O—CH(CH₃)—CO—Q group]

| Compound No. | X | Q | Physical data |
|---|---|---|---|
| 8.9 | Cl | F | |
| 8.10 | Br | Cl | |
| 8.11 | F | Cl | |
| 8.12 | CF₃ | Cl | |

TABLE 9

[Structure: X and NO₂ substituted pyridine connected via O to phenyl-OH]

| Compound No. | X | Physical data |
|---|---|---|
| 9.1 | Cl | m.p. 125–126° C. |
| 9.2 | Br | |
| 9.3 | F | |
| 9.4 | CF₃ | |

TABLE 10

[Structure: X and NH₂ substituted pyridine connected via O to phenyl-OH]

| Compound No. | X | Physical data |
|---|---|---|
| 10.1 | Cl | m.p. 174° C. |
| 10.2 | Br | |
| 10.3 | F | |
| 10.4 | CF₃ | |

TABLE 11

[Structure: X and F substituted pyridine connected via O to phenyl-OH]

| Compound No. | X | Physical data |
|---|---|---|
| 11.1 | Cl | m.p. 97–98° C. |
| 11.2 | Br | |
| 11.3 | F | |
| 11.4 | CF₃ | |

FORMULATION EXAMPLES

Example F1

Formulation Examples for liquid active ingredients of formula I (throughout, percentages are by weight)

| (a) Emulsifiable concentrates | a | b | c |
|---|---|---|---|
| a compound of formula I | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (b) Solutions | a | b | c | d |
|---|---|---|---|---|
| a compound of formula I | 80% | 10% | 5% | 95% |
| ethylene glycol monomethyl ether | 20% | — | — | — |
| polyethylene glycol (MG 400) | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| (c) Granulates | a | b |
|---|---|---|
| a compound of formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | a | b |
|---|---|---|
| a compound of formula I | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Example F2

Formulation examples for solid compound of the formula I (throughout, percentages are by weight)

| (a) Wettable powders | a | b | c |
|---|---|---|---|
| a compound of formula I | 20% | 60% | 0.5% |
| sodium lignosulfonate | 5% | 5% | 5% |
| sodium lauryl sulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | a | b |
|---|---|---|
| a compound of formula I | 10% | 1% |
| octylphenol polyethlene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | a | b | c |
|---|---|---|---|
| a compound of formula I | 5% | 8% | 0.1% |
| talcum | 95% | — | 99.9% |
| kaolin | — | 92% | — |

Ready-for-use dusts are obtained by mixing the active ingredient with the carriers, and grinding the mixture in a suitable mill.

| (d) Extruder granulate | a | b |
|---|---|---|
| a compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| a compound of formula I | 3% |
| polyethylene glycol (MG 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | a | b |
|---|---|---|
| a compound of formula I | 40% | 5% |
| ethylene glycol | 10% | 10% |
| nonylphenol polyethylene glycol | 6% | 1% |

| -continued | | |
|---|---|---|
| (f) Suspension concentrate | a | b |
| (15 moles of ethylene oxide) sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

BIOLOGICAL EXAMPLES

For purposes of comparison the test results obtained with compound A $$Cl \cdots N \cdots O \cdots O-CH(CH_3)-CO-N(CH_3)_2 \quad (A)$$

known from DE-OS No. 3 004 770, page 12, no. 58, are appended to the results of Biological Examples B1 and B2.

Example B1

Preemergence herbicidal action

In a greenhouse, immediately after sowing the test plants in seed dishes, the surface of the soil is treated with an aqueous dispersion of the test compounds, obtained from a 25% emulsifiable concentrate or from a 25% wettable powder with test compounds, which, on account of their insufficient solubility, cannot be formulated to emulsifiable concentrates. Two different concentration series were used, corresponding to 1 and 0.5 kg of test compound per hectare respectively. The seed dishes are kept in the greenhouse at 22°–25° C. and 50–70% relative humidity. The test is evaluated 3 weeks later in accordance with the following rating:

1 = plants have not germinated or are totally withered
2–3 = very strong action
4–6 = average action
7–8 = slight action
9 = no action In this test, the tested compounds of formula I were most effective against monocot grass weeds, whereas no or only insignificant damage was caused to cultivated plants such as wheat, barley, sugar beet, soybeans and cotton at the given rates of application. The comparison compound A is virtually ineffective.

Results:

| Test plant | 1.1 kg/ha | | 1.2 kg/ha | | 1.3 kg/ha | | 1.4 kg/ha | | 1.5 | | 1.6 | | 3.3 kg/ha | | 3.4 kg/ha | | 3.17 kg/ha | | 3.18 kg/ha | | A kg/ha | |
|---|---|---|---|---|---|---|---|---|---|---|---|---|---|---|---|---|---|---|---|---|---|---|
| | 1 | 0.5 | 1 | 0.5 | 1 | 0.5 | 1 | 0.5 | 1 kg/ha | 0.5 kg/ha | 1 kg/ha | 0.5 kg/ha | 1 | 0.5 | 1 | 0.5 | 1 | 0.5 | 1 | 0.5 | 1 | 0.5 |
| Lolium | 1 | 1 | 1 | 2 | 1 | 2 | 1 | 2 | 1 | 1 | 1 | 3 | 7 | 9 | 5 | 8 | 3 | 3 | 2 | 4 | 9 | 9 |
| Alopecurus | 1 | 1 | 1 | 1 | 1 | 2 | 2 | 2 | 1 | 2 | 2 | 4 | 4 | 4 | 3 | 4 | 1 | 2 | 1 | 2 | 8 | 9 |
| Digitaria | 1 | 1 | 1 | 1 | 1 | 1 | 1 | 1 | 1 | 1 | 2 | 1 | 2 | 4 | 1 | 1 | 1 | 1 | 1 | 1 | 4 | 6 |
| Echinochloa | 1 | 1 | 1 | 2 | 1 | 1 | 1 | 1 | 1 | 1 | 1 | 3 | 2 | 2 | 2 | 6 | 1 | 1 | 1 | 1 | 9 | 9 |
| Sorghum | 1 | 1 | 1 | 1 | 1 | 1 | 1 | 1 | 1 | 1 | 1 | 2 | 1 | 3 | 2 | 7 | 1 | 3 | 1 | 2 | 9 | 9 |
| Rottboellia | 1 | 1 | 1 | 1 | 1 | 1 | 1 | 1 | 1 | 1 | 1 | 2 | 2 | 6 | 3 | 7 | 4 | 4 | 1 | 2 | 8 | 9 |
| soybeans | 9 | 9 | 7 | 7 | 9 | 9 | 9 | 9 | | | | | | | | | | | | | | |
| cotton | 9 | 9 | 9 | 9 | 9 | 9 | 9 | 9 | | | | | | | | | | | | | | |
| sugar beet | 9 | 9 | 9 | 9 | 9 | 9 | 9 | 9 | | | | | | | | | | | | | | |

-continued

| Test plant | 1.1 kg/ha 1 | 1.1 kg/ha 0.5 | 1.2 kg/ha 1 | 1.2 kg/ha 0.5 | 1.3 kg/ha 1 | 1.3 kg/ha 0.5 | 1.4 kg/ha 1 | 1.4 kg/ha 0.5 | 1.5 1 kg/ha | 1.5 0.5 kg/ha | 1.6 1 kg/ha | 1.6 0.5 kg/ha | 3.3 kg/ha 1 | 3.3 kg/ha 0.5 | 3.4 kg/ha 1 | 3.4 kg/ha 0.5 | 3.17 kg/ha 1 | 3.17 kg/ha 0.5 | 3.18 kg/ha 1 | 3.18 kg/ha 0.5 | A kg/ha 1 | A kg/ha 0.5 |
|---|---|---|---|---|---|---|---|---|---|---|---|---|---|---|---|---|---|---|---|---|---|---|
| barley | | | | | | | | | 7 | 9 | 7 | 8 | 9 | 9 | 8 | 9 | 8 | 9 | 8 | 9 | 9 | 9 |
| wheat | | | | | | | | | 6 | 8 | 8 | 9 | 8 | 9 | 7 | 9 | 4 | 4 | 3 | 5 | 9 | 9 |

Example B2

Postemergence herbicidal action (Contact herbicide)

A large number of weeds and cultivated plants, both mono- and dicotyledonous, are sprayed postemergence in the 4- to 6-leaf stage with an aqueous active ingredient dispersion in rates of 0.25, 0.5 and 1 kg of test compound per hectare and kept at 24°–26° C. and 45–60% relative humidity. The test was evaluated at least 15 days after treatment in accordance with the same rating as employed in the preemergence test.

In this test, the compounds of formula I were also most effective against monocot grass weeds. The cultivated plants such as wheat, barley, sugar beet, cotton and soybeans were either not damaged or only damaged at higher rates of application of compound. The comparison compound A is virtually ineffective.

X is fluorine, chlorine, bromine, iodine or trifluoromethyl, and

Z is nitrogen.

2. A compound according to claim 1, wherein R is hydrogen or $C_1$–$C_4$alkyl.

3. A compound according to claim 2, wherein R is $C_1$–$C_4$alkyl.

4. A herbicidal composition which comprises, as active ingredient, 0.1 to 80% of a 2-phenoxypropionamide of the formula

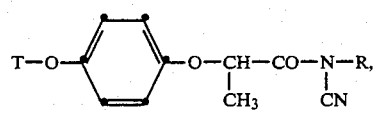

wherein

| Test plant | 1.1 kg/ha 1 | 1.1 kg/ha 0.5 | 1.2 kg/ha 1 | 1.2 kg/ha 0.5 | 1.3 kg/ha 1 | 1.3 kg/ha 0.5 | 1.4 kg/ha 1 | 1.4 kg/ha 0.5 | 1.5 1 kg/ha | 1.5 0.5 kg/ha | 1.6 1 kg/ha | 1.6 0.5 kg/ha | 3.3 kg/ha 1 | 3.3 kg/ha 0.5 | 3.4 kg/ha 1 | 3.4 kg/ha 0.5 | 3.17 kg/ha 1 | 3.17 kg/ha 0.5 | 3.18 kg/ha 1 | 3.18 kg/ha 0.5 | A kg/ha 1 | A kg/ha 0.5 |
|---|---|---|---|---|---|---|---|---|---|---|---|---|---|---|---|---|---|---|---|---|---|---|
| Lolium | 1 | 2 | 2 | 3 | 2 | 2 | 3 | 3 | 2 | 2 | 4 | 5 | 1 | 2 | 3 | 3 | 1 | 1 | 1 | 2 | 7 | 9 |
| Alopecurus | 1 | 2 | 2 | 3 | 1 | 2 | 2 | 6 | 1 | 2 | 4 | 8 | 2 | 2 | 1 | 1 | 1 | 1 | 1 | 2 | 9 | 9 |
| Digitaria | 1 | 1 | 1 | 1 | 1 | 1 | 1 | 1 | 1 | 1 | 1 | 2 | 1 | 1 | 1 | 1 | 1 | 1 | 1 | 1 | 5 | 8 |
| Echinochloa | 1 | 1 | 1 | 1 | 1 | 1 | 1 | 1 | 1 | 1 | 1 | 1 | 1 | 1 | 1 | 1 | 1 | 1 | 1 | 1 | 8 | 9 |
| Sorghum | 1 | 1 | 1 | 1 | 1 | 1 | 1 | 2 | 1 | 1 | 1 | 3 | 1 | 1 | 1 | 1 | 1 | 1 | 1 | 1 | 8 | 9 |
| Rottboellia | 1 | 1 | 1 | 2 | 1 | 1 | 1 | 2 | 1 | 1 | 1 | 3 | 1 | 1 | 1 | 1 | 1 | 1 | 1 | 1 | 6 | 9 |
| Avena | | | | | | | | | 1 | 2 | 2 | 5 | | | | | | | | | | |
| soybeans | 9 | 9 | 9 | 9 | 6 | 9 | 9 | 9 | | | | | 9 | 9 | 7 | 8 | 8 | 8 | 8 | 9 | 7 | 9 |
| cotton | 7 | 9 | 9 | 9 | 8 | 8 | 9 | 9 | | | | | 8 | 9 | 8 | 9 | 7 | 9 | 8 | 8 | 7 | 9 |
| sugar beet | 8 | 9 | 8 | 9 | 8 | 8 | 8 | 9 | | | | | 8 | 9 | 8 | 9 | 7 | 8 | 8 | 8 | 8 | 9 |
| barley | | | | | | | | | 3 | 7 | 9 | 9 | | | | | | | | | | |
| wheat | | | | | | | | | 8 | 9 | 9 | 9 | | | | | | | | | | |

What is claimed is:

1. A 2-phenoxypropionic acid cyanamide of the formula

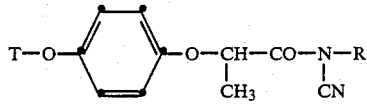

wherein

R is hydrogen, $C_1$–$C_4$alkyl, $C_3$–$C_4$alkenyl, $C_3$–$C_4$alkynyl or $C_2$–$C_4$alkoxyalkyl, and T is a quinoxalinyl radical of the formula

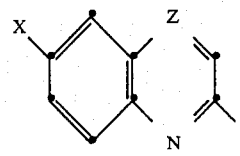

wherein

R is hydrogen, $C_1$–$C_4$alkyl, $C_3$–$C_4$alkenyl, $C_3$–$C_4$alkynyl or $C_2$–$C_4$alkoxyalkyl, and T is a quinoxalinyl radical of the formula

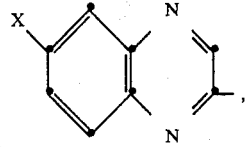

wherein X is fluorine, chlorine, bromine, iodine or trifluoromethyl, in combination with conventional carriers or other adjuvants.

5. A Method of controlling weeds in crops of cultivated plants, which method comprises applying, either pre- or postemergence, a herbicidally effective amount of a compound of the formula

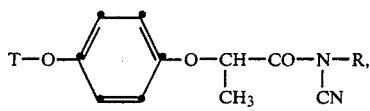

wherein
R is hydrogen, $C_1$-$C_4$-alkyl, $C_3$-$C_4$alkenyl, $C_3$-$C_4$-alkynyl or $C_2$-$C_4$alkoxyalkyl, and
T is a quinoxalinyl radical of the formula

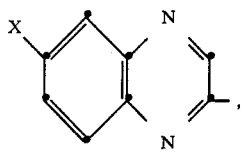

wherein X is fluorine, chlorine, bromine, iodine or trifluoromethyl to the cultivated area.

6. A compound according to claim 1, wherein X is fluorine or chlorine.

7. A method according to claim 5 of selectively controlling weeds.

8. A method according to claim 7 of selectively controlling monocot weeds.

9. A compound according to claim 1, wherein R is $C_1$-$C_4$alkyl and T is 6-fluoroquinoxalin-2-yl.

10. A compound according to claim 1, wherein R is $C_1$-$C_4$alkyl and T is 6-chloroquinoxalin-2-yl.

11. A method according to claim 8 of selectively controlling monocot weeds pre- or postemergence in crops of useful plants.

12. A method according to claim 11, wherein the crops of useful plants are dicots selected from soybeans, rape, sugar beet and cotton.

13. 2-[4-(6-Chloroquinoxalin-2-yloxy)phenoxy]propionic acid N-cyano-N-methylamide according to claim 1.

14. 2-[4-(6-Fluoroquinoxalin-2-yloxy)phenoxy]propionic acid N-cyano-N-ethylamide according to claim 1.

15. 2-[4-(6-Fluoroquinoxalin-2-yloxy)phenoxy]propionic acid N-cyano-N-methylamide according to claim 1.

16. 2-[4-(6-Chloroquinoxalin-2-yloxy)phenoxy]propionic acid N-cyano-N-ethylamide according to claim 1.

* * * * *